United States Patent [19]

Lowell

[11] 4,170,129

[45] Oct. 9, 1979

[54] METHOD OF DETERMINING PORE VOLUME DISTRIBUTION OF A POWDER SAMPLE BY MERCURY INTRUSION

[76] Inventor: Seymour Lowell, 42 Wood Hollow Rd., Albertson, N.Y. 11507

[21] Appl. No.: 886,731

[22] Filed: Mar. 15, 1978

[51] Int. Cl.² ............................................. G01N 15/08
[52] U.S. Cl. .......................................................... 73/38
[58] Field of Search ................................ 73/38, 37, 73

[56] References Cited

U.S. PATENT DOCUMENTS

| 3,073,357 | 1/1963 | Hampton | 73/38 X |
| 3,199,341 | 8/1965 | Heuer, Jr. et al. | 73/38 X |
| 3,388,586 | 6/1968 | Golmard et al. | 73/38 |

*Primary Examiner*—Jerry W. Myracle
*Attorney, Agent, or Firm*—Bauer & Amer

[57] ABSTRACT

As understood, the effectiveness of using mercury penetration or intrusion into a powder sample to measure the pore volume distribution thereof is based on negative capillarity, i.e. that a porous solid will repulse a non-wetting liquid, such as mercury, except as the mercury is forced into the pores thereof by pressure. Whereas in the prior art the mercury is intruded into the powder sample at pressures in an ascending order, but with gaps therebetween and thus according to a "discontinuous" pressure pattern, the within inventive method practices the mercury intrusion technique according to an ascending pressure pattern that is "continuous". The pore volume distribution curve produced by the within inventive method is thus more accurate than that of prior art data-gathering methods, since it is produced without interpolation between curve-plotting data points.

2 Claims, 4 Drawing Figures

| PRESSURE PSIA | DIAMETER OF INTRUDED PORE μm | PELLETED ACTIVATED CHARCOAL- .9100 g. SAMPLE WEIGHT PENETRATION c.c. |
|---|---|---|
| 1 | 175 | 0.0 |
| 5 | 35 | .007 |
| 10 | 17.5 | .020 |
| 14.7 | 11.22 | .032 |
| 19.4 | 9.0 | .032 |
| 50 | 3.5 | .036 |
| 100 | 1.75 | .044 |
| 500 | .35 | .064 |
| 1,000 | .175 | .067 |
| 5,000 | .035 | .084 |
| 10,000 | .0175 | .096 |
| 15,000 | .012 | .105 |
| 20,000 | .00875 | .112 |
| 30,000 | .006 | .128 |
| 40,000 | .004375 | .141 |
| 50,000 | .0035 | .154 |
| 60,000 | .003 | .168 |

METHOD OF DETERMINING PORE VOLUME DISTRIBUTION OF A POWDER SAMPLE BY MERCURY INTRUSION

The present invention relates to an improved operating mode for a mercury intrusion porosimeter, and more particularly to a method of data-gathering using mercury intrusion that results in a direct and more accurate determination of the pore size distribution of a test powder sample.

As understood, the typical operating pressures applied during use of a mercury intrusion porosimeter may range from "1" to "60,000" psia. Understandably therefore, current practice dictates proceeding from one pressure level to an adjacent or next higher level spaced therefrom, the spacings or intervals therebetween varying from "100" to "500" or more pounds per square inch. To select operating pressures at closer intervals would be extremely burdensome, if the entire pressure range is to be covered. Yet, because the operating pressures are at spaced intervals or according to a "discontinuous" pattern, the plotted curve of the pore volume distribution between data points, i.e. those curve portions coextensive with said intervals between actual operating pressures, are the result of interpolation and not actual measurement of the test sample. To this extent therefore, current practice is vulnerable to error and inaccuracies.

Broadly, it is an object of the present invention to provide a method of data-gathering using mercury intrusion that is applied according to an ascending "continuous" pressure pattern, thus overcoming the foregoing and other shortcomings of the prior art. Specifically, it is an object to intrude the mercury under a pressure of an ascending nature throughout a selected range, with intervals or discontinuities therein, while continuously measuring the test sample at all pressure levels throughout the entire pressure range, thereby contributing to obtaining a determination of the pore volume distribution of a test powder sample of significantly enhanced accuracy.

A method of determining the pore volume distribution of a powder sample demonstrating objects and advantages of the present invention is one that contemplates intruding mercury into said powder sample, and includes the steps of placing the mercury in intruding relation to the powder sample and arranging a mercury-displacing member or piston for movement along a delineated movement path. The piston, however, is advanced not by conventional sliding thereof but by rotation of its threadably engaged piston rod. Thus, the rotation amounts to a continuously unthreading of the mercury-displacing piston, one thread at a time, along the movement path, thereby causing intrusion of the mercury into the powder sample in a continuous ascending pressure pattern.

The above brief description, as well as further objects, features and advantages of the present invention, will be more fully appreciated by reference to the following detailed description of the theoretical basis and of illustrative apparatus for practicing the method of the present invention, the same being illustrated in the accompanying drawings as follows.

DATA-GATHERING USING MERCURY INTRUSION

Various models of mercury intrusion porosimeters are in use to provide data for determining the pore volume distribution of a powder sample typically destined for use in the manufacturing of filters, adsorbents, catalysts, porous rock separators, etc. The need for defining pore structures of materials in the applications mentioned is widely recognized. In the case of sintered metal and ceramic parts, for example, structural failure can be anticipated if they have excessive pores, whereas materials used for catalysts must have open and accessible pores, provided they are of a uniform size, if they are to function properly.

Figures 1, 2:
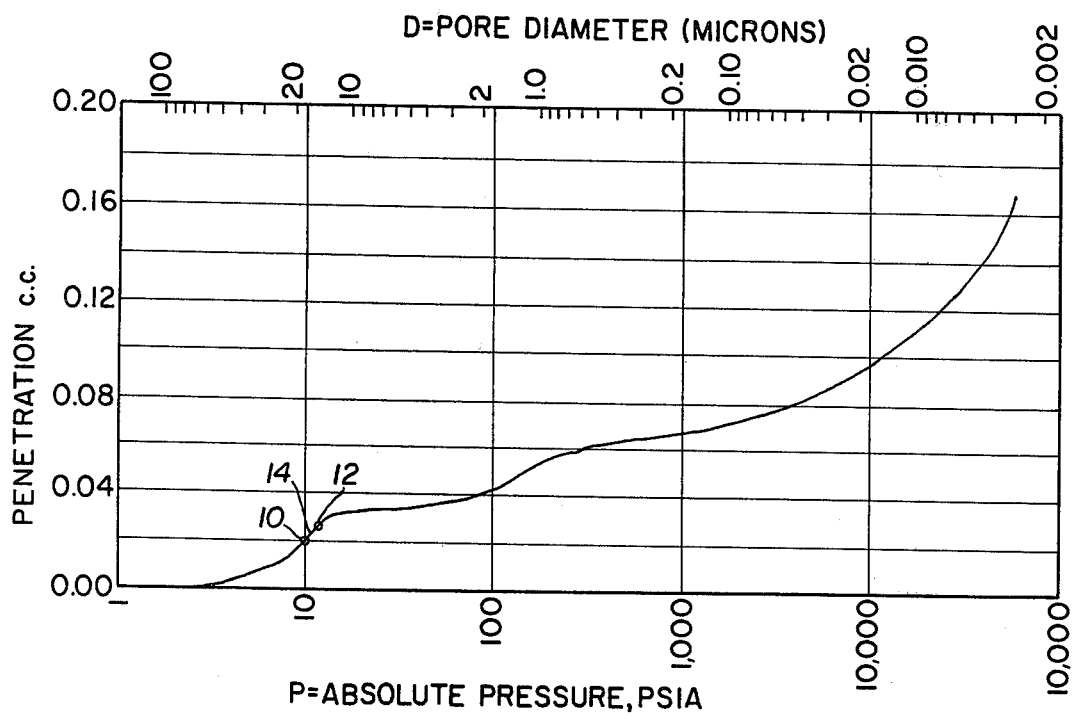
FIG. 1 illustrates the relation between pressures selected for the intruding of mercury into a powder sample and the pore size thereof corresponding therewith, and also a typical pore volume distribution of a selected powder sample.
FIG. 2 is the resulting plotted curve using the data of FIG. 1.

Using the technique of mercury intrusion has proven invaluable in evaluating the pore structure or distribution of materials in particulate or powder form. As understood, the theoretical basis for mercury penetration or intrusion is negative capillarity. That is, it is known that a porous solid will normally repulse a non-wetting liquid, of which mercury is a prime example, from the surfaces thereof. Thus, pressure is required to cause a non-wetting liquid like mercury to enter any pore. Further, the well known relationship between the sizes or diameters of pores and the required penetrating pressures is readily determinable. In this connection, reference should be had to FIG. 1, and more particularly, to the left and middle columns thereof in which there is set forth the required pressures in pounds per square inch absolute (psia) required for effectively intruding mercury into correspondingly sized pores, expressed in microns. The right-hand column of FIG. 1 illustrates the pore volume distribution for the selected material "pelletted activated charcoal". Thus, mercury at 10 psi will intrude into pores of 17.5 microns and, as illustrated in the selected FIG. 1 sample of pelletted activated charcoal, there is a volume of 0.020 cubic centimeters (c.c.) of this diameter size of pore. The curve plot point represented by the data just noted is designated by the reference numeral 10 in FIG. 2. As will be explained in greater detail subsequently, the next pressure level that is typically selected for the intrusion of mercury is "14.7 psia" which, mathematically, has a cooperative relationship with a pore size diameter of "11.22 microns". Again assuming that the selected powder sample is said FIG. 1 pelletted activated charcoal, this material is shown to have a density of said 11.22 micron-sized pores amounting to a total volume of 0.32 c.c.'s and thus provides the plot point designated 12 in FIG. 2.

At this point in the description it is significant to note that the pressure levels at which the mercury is intruded, as set forth in the left-hand column of FIG. 1, is not continuous, but rather consists of selected levels having gaps therebetween. As clearly illustrated in FIG. 1, the size of the gaps between adjacent pressure levels are of increasing magnitude in the ascending direction of the pressure pattern. Thus, whereas there is only a 50 pound per square inch difference between pressure level "50" and pressure level "100", the difference between the "100" pressure level and its next higher level or "500", is 400 pounds per square inch. The obvious practical reason for the gaps between adjacent pressure levels is that going from a starting pressure of "1" to a terminal pressure of "60,000" would be a burdensome procedure if it was conducted at comparatively small ascending increments. It is undoubtedly for this reason that the density or volume of the various diameter-sized pores of a sample are measured at discontinuous pressure levels despite the recognition that the data can only be interpolated at in-between pressure levels, and to this extent may not therefore be totally accurate. In other words, and again referring to FIG. 2, the portion of the plotted curve designated 14 which is drawn between plot points 10 and 12 is merely assumed to be as illustrated, and is not dictated by actual data obtained from measurement of the powder sample using the mercury intrusion technique.

THE METHOD OF THE PRIOR ART APPARATUS

Figure 3:
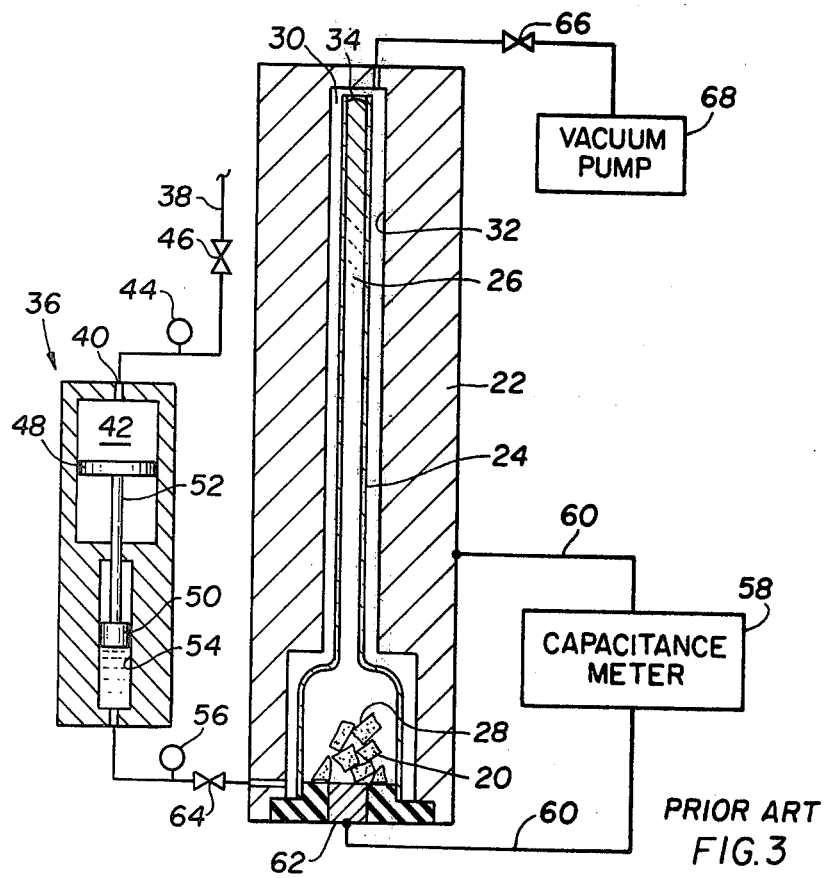
FIG. 3 is a diagrammatic illustration of the prior art apparatus and arrangement thereof for obtaining the FIG. 1 data.

Reference is now made to FIG. 3 which diagrammatically illustrates the apparatus and the manner in which it was set up in relation to a powder sample 20 for developing the data set forth in FIG. 1 from which, as already noted, the plotted curve of FIG. 2 is typically prepared. For purposes of providing a background for understanding the significance of the improvements of the within inventive method, it suffices to illustrate said prior art apparatus diagrammatically in FIG. 3 and to note only its salient structural features and mode of operation. In an appropriate pressure housing 22 there is provided a glass capillary 24, the stem of which is filled with an appropriate volume of mercury 26 which, as at 28, is in surface contact with, and thus in intruding relation to, the previously noted powder sample 20. As understood, an incompressible fluid 32, such as hydraulic oil, fills the annular space 30 about the capillary 24 within the housing 22, with the result that the fluid 32, as at the interface 34, is in pushing contact with the mercury 26.

To provide the various selected levels of pressure at which the mercury 26 is intruded into the powder sample 20, the prior art makes use of a so-called pressure multiplier, generally designated 36. This unit has an operative conduit connection 38 to an appropriate pressure source, such as pressure air, and at its opposite end, as at 40, is connected to direct the pressure fluid into a piston chamber 42 at a selected pressure level appropriately measured by a pressure gauge 44. Valve 46 assists in a well understood manner in achieving flow of the pressure fluid into the chamber 42 at the required pressure level. In chamber 42 the pressure fluid acts against the large diameter piston 48, thus causing movement therein and, more important, corresponding movement under an amplified pressure in small diameter piston 50 connected by rod 52 in depending relation from piston 48. Descending movement 50 in piston chamber 54, which chamber will be understood to be filled with the incompressible fluid 30 results, in a well understood manner, in pressure, at a level measured by gauge 56, being exerted via the fluid 30 against the mercury 26. As a consequence, a portion of the mercury 26 intrudes into the powder sample 20.

As understood, the volume of the mercury intruded into the powder sample 20 changes the electrical characteristics thereof, and this is readily measured by a capacitance meter 58 having conductors 60 electrically connected to housing 22 and to a mercury contact electrode 62. Since the amount or volume of intruded mercury is a function of the change in capacitance of the sample 20, it necessarily follows that measurements of the latter readily provide an indication of the amount of mercury penetrating or intruding into the powder sample 20.

For completeness sake it is noted that the prior art apparatus includes means for properly preparing the sample 20 for application of the mercury intrusion technique, the same including a valve 64 for temporarily isolating the pressure multiplier 36 from the housing 22 while valve 66 is in communication with a vacuum pump 68 so that any air in the capillary 24 can be evacuated prior to back-filling the same with mercury. The applied vacuum is, of course, also effective in removing air from the clearance 32 prior to the filling of this space with the hydraulic fluid 30. After preparation of the powder sample 20 and the mercury 26 in a well understood manner, valve 66 is of course closed and valve 64 opened, and the pressure manipulator 36 then operated in a manner already described. More particularly, unit 36 is operated to produce intrusion of the mercury at the specified pressure levels indicated in FIG. 1 so as to obtain data points, as exemplified by points 10 and 12, for the subsequent plotting of the pore volume distribution of the powder sample as set forth in FIG. 2.

THE IMPROVED INVENTIVE METHOD HEREOF

Figure 4:
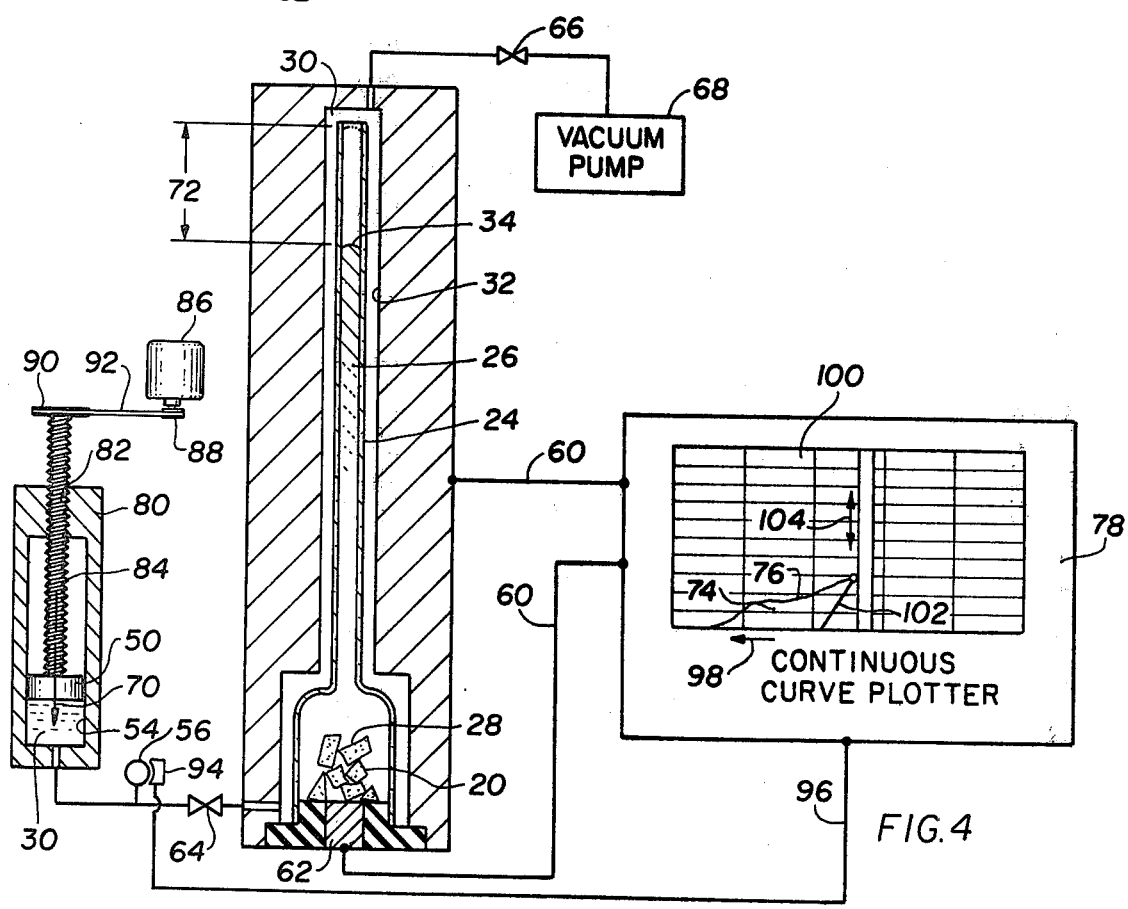
FIG. 4 is a diagrammatic illustration of apparatus for practicing the within improved inventive data-collecting procedure or method hereof, said collected data contributing to the producing of a plotted curve of a pore volume distribution of the powder sample.

The recommended apparatus for practicing the improved inventive method hereof is diagrammatically illustrated in FIG. 4. To avoid the need to repeat the description of structure already described in connection with the prior art apparatus of FIG. 3 and also used in apparatus recommended for practicing the method of the present invention, the same reference numerals are utilized to designate these common structural features. Underlying the present invention is the recognition that the mercury intrusion technique contemplates intrusion of the mercury initially in the large-sized diameter pores and subsequently in pores of progressively diminishing extent. This in turn requires an inverse pressure pattern, i.e. a pattern that is of a progressively ascending order. In this regard, therefore, as long as the pressure applying piston 50 is advanced through a power stroke in relation to the piston chamber 54 or, more particularly, in pushing contact against the hydraulic fluid 30 in that chamber, there will result the necessary pressure pattern of an ascending order to, in turn, cause the successive intrusion of mercury in diameter-sized pores of a progressively diminishing extent. Another way of expressing this is that underlying the present invention is the recognition that if movement can be imparted to piston 50 in a "continuous" manner, that this of necessity would also provide a pressure pattern in the intruding mercury 26, delivered via the hydraulic fluid 30, that would also be of a corresponding "continuous" nature. Thus, if the pressure pattern of the intruded mercury is continuous, as distinguished from being discontinuous with selected gaps therebetween, as exemplified by the prior art plot points 10 and 12 previously discussed in connection with FIG. 2, the density of the powder sample 20 could then be measured more accurately using the mercury intrusion technique.

To achieve continuous displacement of the hydraulic fluid 30 from the chamber 54, the present inventive method contemplates controlling the movement of piston 50 along movement path 70 such that it proceeds in a "continuous" fashion, thereby contributing to an operating pressure pattern at which the mercury is intruded into the powder sample which, as already noted, also is correspondingly "continuous".

In terms of its function, the piston 50 is a mercury-displacing means since, acting through the hydraulic fluid 30, its descending movement along the movement path 70 is effective in causing the necessary intrusion or penetration of the mercury 26 into the powder sample 20. That is, as shown in FIG. 4, the initial height of the mercury column 26 in the capillary 24, as illustrated in phantom perspective, is diminished by the force exerted against it by the hydraulic fluid 30 to the subsequent illustrated position, shown in full line perspective, thus signifying that as a result of the mercury intrusion procedure a volume 72 of the mercury has been intruded or caused to be penetrated into the powder sample 20. As understood, and as will be more apparent subsequently, said volume 72 of mercury is also the integrated area of the plotted curve of FIG. 2, and also the area designated 74 of the curve 76 directly produced by the continuous curve plotter 78.

In accordance with the present invention, the within inventive method is effectively practiced by having the piston 50 operatively arranged for movement along the path 70 within a housing 80. Strategically located in bounding relation to, and thus along the path 70, is a threaded through bore 82 in the upper portion of the housing 80, with which threaded engagement is established by having the piston 50 mounted on a cooperating threaded rod 84. In practice, good results have been achieved using 7/8 inch diameter threads, provided 14 to the inch, along the threaded rod 84, and threads of a cooperating pitch and size for the threaded through bore 82. To power the rod 84 in rotation, and thus to cause uniform unthreading thereof in relation to the threaded opening 82 so that piston 50 advances in uniform increments along the movement path 70, there is provided a motor 86. In the drive connection illustrated, a pulley 88 is mounted on the shaft of motor 86 while a pulley 90 is mounted on the upper end of threaded rod 84, and a closed loop pulley belt 92 is entrained about these pulleys so that the rotational power of the motor 86 is effectively transmitted to the threaded rod 84.

In sharp contrast to the prior art in which discontinuous plot points, as exemplified by points 10 and 12, are obtained of the powder sample from which the pore volume distribution in the form of a curve is then manually plotted, as illustrated in FIG. 2, the within inventive method contemplates the use of a continuous curve plotter 78, and thus the direct print-out of the pore volume distribution curve 76. This possibility is afforded since, as already noted, the mercury displacement is in small increments which for all practical purposes is "continuous", and thus the ascending pressure pattern exerted against the mercury, as measured by the pressure gauge 56, is also correspondingly in very small increments and is therefore also for all practical purposes of a "continuous" nature. As diagrammatically illustrated in FIG. 4, the continuous ascending pressure pattern of the intruded mercury is registered, for example, on the pressure gauge 56 and supervised by an appropriate sensor 94 and transmitted as an electrical signal or the like via the conductor 96 to any one of a number of commercially available continuous curve plotters, designated 78, and will thus produce, in a well understood manner, movement 98 at an appropriate rate in graph paper beneath the printing tip of a stylus 102. The other component necessary to produce the curve 76, or namely descending or ascending movement 104 in the stylus 102, is produced by measuring the change in capacitance as a result of mercury intruded into the powder sample 20, as already described in connection with FIG. 3. Specifically, the change in capacitance is transmitted, again preferably as an electrical signal via the conductors 60 to the curve plotting unit 78. As a result of graph paper movement 98 and of the stylus movement 104, the pore volume distribution curve 76 of the powder sample 20 is produced directly on the graph paper 100 in accordance with the known and well understood operation of the continuous curve plotter 78. For completeness sake, it is noted that favorable results have been achieved with the inventive method hereof using a continuous curve plotter 78 manufactured by Esterline Angus Instrument Corp. of Lodi, New Jersey.

From the foregoing it should be readily appreciated that there has been described herein an improved method of using the mercury intrusion technique in relation to a powder sample to obtain a more accurate pore volume distribution in that the successive pressure levels at which the mercury is intruded is in such small increments of an ascending nature that for all practical purposes it is "continuous", and therefore has a mode of operation that is a compatible input to a continuous curve plotter 78.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. A method of determining the pore volume distribution of a powder sample by intruding mercury into said powder sample, said method comprising the steps of placing said mercury in intruding relation to said powder sample, arranging for movement along a delineated movement path of a mercury-displacing means disposed in pushing relation to said mercury, bounding said delineated movement path and embodying said mercury-displacing means with intermeshing threads, continuously unthreading said mercury-displacing means from said path-bounding threads incident to causing intrusion of said mercury into said powder sample, obtaining measurements of the continuously ascending pressure pattern of said mercury-displacing means resulting from said unthreading, and operating a continuous curve plotter using said measurements, whereby said mercury intrusion into said powder sample is in said aforesaid continuous ascending pressure pattern and is produced as a plotted curve of the pore volume distribution of said powder sample.

2. The method of determining pore volume distribution of a powder sample by mercury intrusion as claimed in claim 1, wherein an incompressible body of hydraulic oil is located in an interposed position between said mercury-displacing means and said mercury to transmit said continuous ascending pressure pattern of said mercury-displacing means continuously advanced along said movement path to said mercury.

* * * * *